(12) United States Patent
Schneider (10) Patent No.: US 7,931,648 B2
(45) Date of Patent: Apr. 26, 2011

(54) SURGICAL GLOVE SYSTEM

(76) Inventor: Andrew I. Schneider, Palm Beach Gardens, FL (US)

( * ) Notice: Subject to any disclaimer, the term of this patent is extended or adjusted under 35 U.S.C. 154(b) by 761 days.

(21) Appl. No.: 11/591,305

(22) Filed: Nov. 1, 2006

(65) Prior Publication Data

US 2007/0192931 A1    Aug. 23, 2007

Related U.S. Application Data (63) Continuation-in-part of application No. 11/335,050, filed on Jan. 19, 2006.

(51) Int. Cl.
*A61B 18/18* (2006.01)
(52) U.S. Cl. ............... 606/45; 362/103; 604/35; 606/49
(58) Field of Classification Search .............. 606/45, 606/49; 2/161.7; 604/35; 362/103
See application file for complete search history.

(56) References Cited

U.S. PATENT DOCUMENTS

| | | | |
|---|---|---|---|
| 2,311,276 A | 2/1943 | Wilcox | |
| 2,847,012 A | 8/1958 | Eastman | |
| 3,735,760 A | 5/1973 | Vreeland, Jr. | |
| 3,845,771 A | 11/1974 | Vise | |
| 3,875,945 A | 4/1975 | Friedman | |
| 4,198,985 A | 4/1980 | Abel | |
| 4,488,726 A | 12/1984 | Murray | |
| 4,510,939 A | 4/1985 | Brenman et al. | |
| 4,620,528 A | 11/1986 | Arraval | |
| 4,932,952 A | 6/1990 | Wojciechowicz, Jr. | |
| 5,120,304 A * | 6/1992 | Sasaki | 604/35 |
| 5,242,440 A * | 9/1993 | Shippert | 606/30 |
| 5,283,722 A * | 2/1994 | Koenen et al. | 362/570 |
| 5,312,400 A | 5/1994 | Bales et al. | |
| 5,673,436 A | 10/1997 | Piper | |
| 5,782,516 A | 7/1998 | Partida | |
| 5,816,676 A | 10/1998 | Koenen Myers et al. | |
| 5,947,922 A | 9/1999 | MacLeod | |
| 6,112,330 A | 9/2000 | Bryan | |
| 6,409,734 B1 | 6/2002 | Zapata | |
| 6,551,312 B2 | 4/2003 | Zhang et al. | |
| 6,567,990 B1 | 5/2003 | Spitznagle | |
| 6,569,163 B2 | 5/2003 | Hata et al. | |
| 6,592,235 B1 | 7/2003 | Mayo | |
| 6,646,855 B2 | 11/2003 | Buening et al. | |
| 6,892,397 B2 | 5/2005 | Raz et al. | |
| 7,012,797 B1 * | 3/2006 | Delida | 361/230 |
| 2004/0154071 A1 | 8/2004 | Frahm | |
| 2004/0260281 A1 | 12/2004 | Baxter et al. | |

FOREIGN PATENT DOCUMENTS

| | | | |
|---|---|---|---|
| GB | 2316429 | * | 8/1996 |
| WO | WO 02/43550 A1 | | 6/2002 |

* cited by examiner

*Primary Examiner* — Linda C Dvorak
*Assistant Examiner* — Jaymi Della
(74) *Attorney, Agent, or Firm* — Duane Morris LLP; J. Rodman Steele, Jr.; Gregory M. Lefkowitz

(57) ABSTRACT

A surgical system including a surgical glove having support systems such as, but not limited to, lights, electrical cautery, suction, and irrigation. The surgical glove may include one or more lights, electrical cautery, suction, and irrigation positioned on distal ends of fingers of the surgical glove. The support systems may be controlled with switches positioned on the fingers upon which each support system is positioned. The switches may be operable with the thumb on the human hand upon which the surgical glove is attached. The surgical system may also include a surgical gown having a connection system for attaching support conduit to the surgical gown. The surgical system enables a surgeon to have a plurality of support systems immediately available and reduces entanglement problems endemic with conventional systems.

22 Claims, 8 Drawing Sheets

SURGICAL GLOVE SYSTEM

CROSS-REFERENCE TO RELATED APPLICATIONS

This application is a continuation-in-part application of U.S. patent application Ser. No. 11/335,050, filed Jan. 19, 2006.

FIELD OF THE INVENTION

This invention is directed generally to surgical systems, and more particularly to surgical systems for providing support to a surgeon during surgery.

BACKGROUND

Currently, the majority of conventional surgical instruments are hand-held and hand, foot, or remotely operated. Surgical instruments such as electrical cautery, suction, and hand-held lights typically include electrical supply cords, fiber optic cords, or conduits that are held in place on a surgical table by fastening the cords with clamps to a surgical top drape positioned on top of a patient. The cords and conduits are arranged on the surgical field so that they can be accessed easily by surgeons, assistants, or nurses. Unfortunately, as well intention and organized as the setup may be, the cords and conduits invariably become entangled during the course of a procedure, thereby creating frequent frustration and time delay. Once entangled, instruments become more difficult to easily reach or to pass between surgeons. Entanglement of instrument wire and cords also shortens the effective working length of the instruments and further interferes with their accurate and unobstructed use.

Often times, the electrical cautery or suction supply is accidentally dropped from the surgical field onto the floor, thereby compromising their sterility and requiring replacement. This occurs more frequently with shower curtains drapes and during the course of long, complex procedures.

Typically, irrigation supplies are stored on a table remote from the surgical field and are handed to the surgeon by a scrub nurse within a bulb syringe, or other container, when requested. Unfortunately, during a procedure, the scrub nurse may be occupied for a variety of reasons and have difficulty providing the irrigation in a timely fashion. For example, a scrub nurse is commonly asked to hold a retractor, or other instrument in the surgical field and is not available to easily turn around and grab the irrigation when needed. Thus, there is a great need for a more efficient, user-friendly system that eliminates entanglement reliably and avoids the problems set forth herein.

SUMMARY OF THE INVENTION

This invention relates to a surgical system that includes a surgical glove having support systems such as, but not limited to, one or more light sources, an electrical cautery device, a suction source, and an irrigation supply. The surgical system may also include a surgical gown. The surgical glove may include one or more of the light sources, electrical cautery devices, suction sources, and irrigation sources positioned on distal ends of fingers of the surgical glove. The support systems may be controlled with switches positioned on the fingers upon which each support system is positioned. The switches may be operable with the thumb from the human hand upon which the surgical glove is attached. The surgical system may also include a surgical gown having a connection system for attaching support conduit supporting the support systems to the surgical gown. The surgical system enables a surgeon to have a plurality of support systems immediately available and eliminates entanglement problems endemic with conventional systems. The support systems may be attached to the surgical glove in numerous configurations to optimize the configuration for a surgeon such that the systems are located for facility of use and in a position where the systems are unlikely to obstruct or conflict with the general use of the surgeon's hand or the use of surgical instruments.

The support systems, including, but not limited to, light sources, electrical cautery devices, suction sources, and irrigation sources, may be coupled to distal, volar, radial, ulnar or dorsal surface locations of the fingers of the surgical glove. In particular, in one embodiment, the light source may be coupled to a distal, dorsal surface of the index or long finger, or both. The electrical cautery device may be coupled to a distal, volar end of the index finger. The suction source may be coupled to a distal, volar radial end of the long finger. The irrigation source may be coupled to a distal, volar radial end of the little finger.

The support systems may be controlled with support control switches adapted for each support system. The support switches may be attached to the fingers upon which the support system is attached and may be easily activated using the thumb on the same hand. For instance, the electrical cautery switch may be positioned on the finger upon which the electrical cautery is attached. The electrical cautery switch may be positioned on the radial aspect of the finger.

The surgical system may also include a surgical gown formed from a body configured to fit on a human torso and first and second sleeves adapted to extend from a shoulder to a wrist portion. The surgical gown may include a connection system configured to attach support conduits to the surgical gown. The surgical gown, in at least one embodiment, may include support control switches that may be attached to any of the support systems.

In one embodiment, the support conduits extend from the dorsal wrist area of the surgical glove along the lateral or ulnar aspect of the surgeon's arm, toward the shoulder, then posteriorly around the shoulder and finally caudally down the surgeon's back, where they will be directly, appropriately connected to the appropriate connections. In an alternative embodiment, the support conduits may extend along medial or radial aspects of the arms, into the axilla of the shoulder, then over the lower region of the scapula and cardally down the surgeon's back. In the first embodiment, the connection system may include attachment devices on lateral aspects of the surgical gown corresponding to a forearm, upper arm, lateral shoulder, scapular, and lower lateral back areas of the surgical gown to retain support conduits extending from the surgical glove, along an arm, over a shoulder, and along a back. The attachment devices effectively, visually and physically, eliminate the independent presence of electrical wires, conduits, and other support conduits, in the surgical field. In addition, the attachment devices assist in preventing accidental entanglement or contamination of these entities without inhibiting the range of motion of a surgeon's arm or shoulder.

The invention may also be directed to a method of performing a surgical procedure in which the need to retrieve surgical implements that beforehand were rested on the surgical field is eliminated. In particular, the method may include attaching a first surgical support system to a person conducting the surgical procedure before commencing the surgical procedure. The person conducting the surgical procedure may be, but is not limited to being, a surgeon or other appropriate person. At least one surgical instrument may be attached to the first surgical support system such that the at least one surgical instrument extends proximate to a hand and at or distal to the wrist of the person to which the first surgical support system is attached. The first surgical support system may remain attached to the person throughout the surgical procedure eliminating need for a surgical implement assistant. For instance, the surgeon need not rest instruments on the surgical field and constantly pick up the instruments or request the instruments from an assistant. Rather, the instruments may remain attached to the surgeon throughout the duration of the surgery. Such a method enables a surgeon to work more independently and thus maintain focus on the surgical procedure.

An advantage of this invention is that the surgical system provides a surgeon with immediate access to support systems without having to retrieve surgical implements that beforehand were rested on the surgical field.

Another advantage of the invention is that the surgical system seemlessly incorporates support systems within a surgical glove in a configuration that does not inhibit a surgeon's range of motion with the surgeon's hands and fingers.

Yet another advantage of this invention is that the surgical system eliminates the possibility of support systems falling from the surgical field onto the floor and thereby necessitating that systems be sanitized or replaced, which delays the operative procedure.

Another advantage of this invention is that a surgeon may control support devices from switches positioned on the surgeon's gloves or gown.

Still another advantage of this invention is that use of the invention eliminates the need for a surgical implement assistant because the surgical implements are attached to the surgeon in a manner that the implements are readily usable by the surgeon.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

Figure 3:
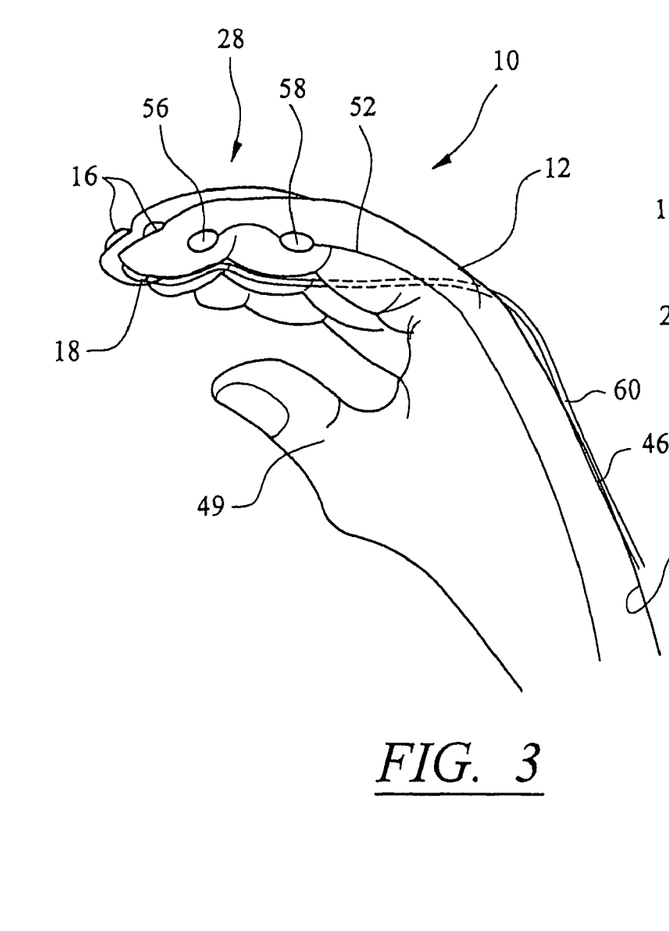
FIG. 3 is a side view of a right hand glove of the surgical system.
Figure 4:
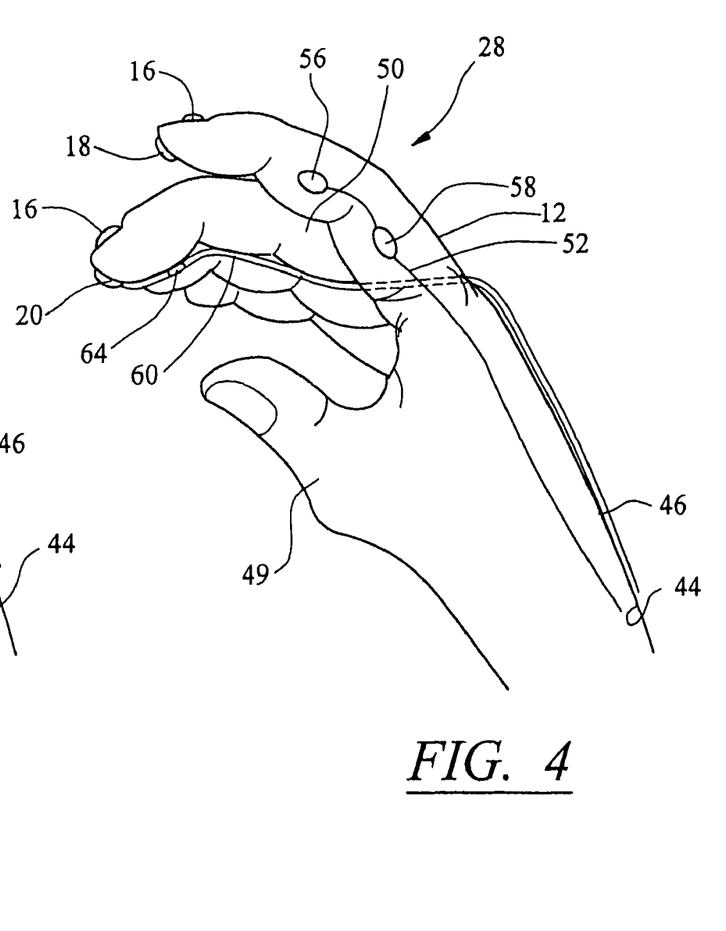
FIG. 4 is a side view of a right hand glove of the surgical system with fingers of the glove in another position.
Figure 5:
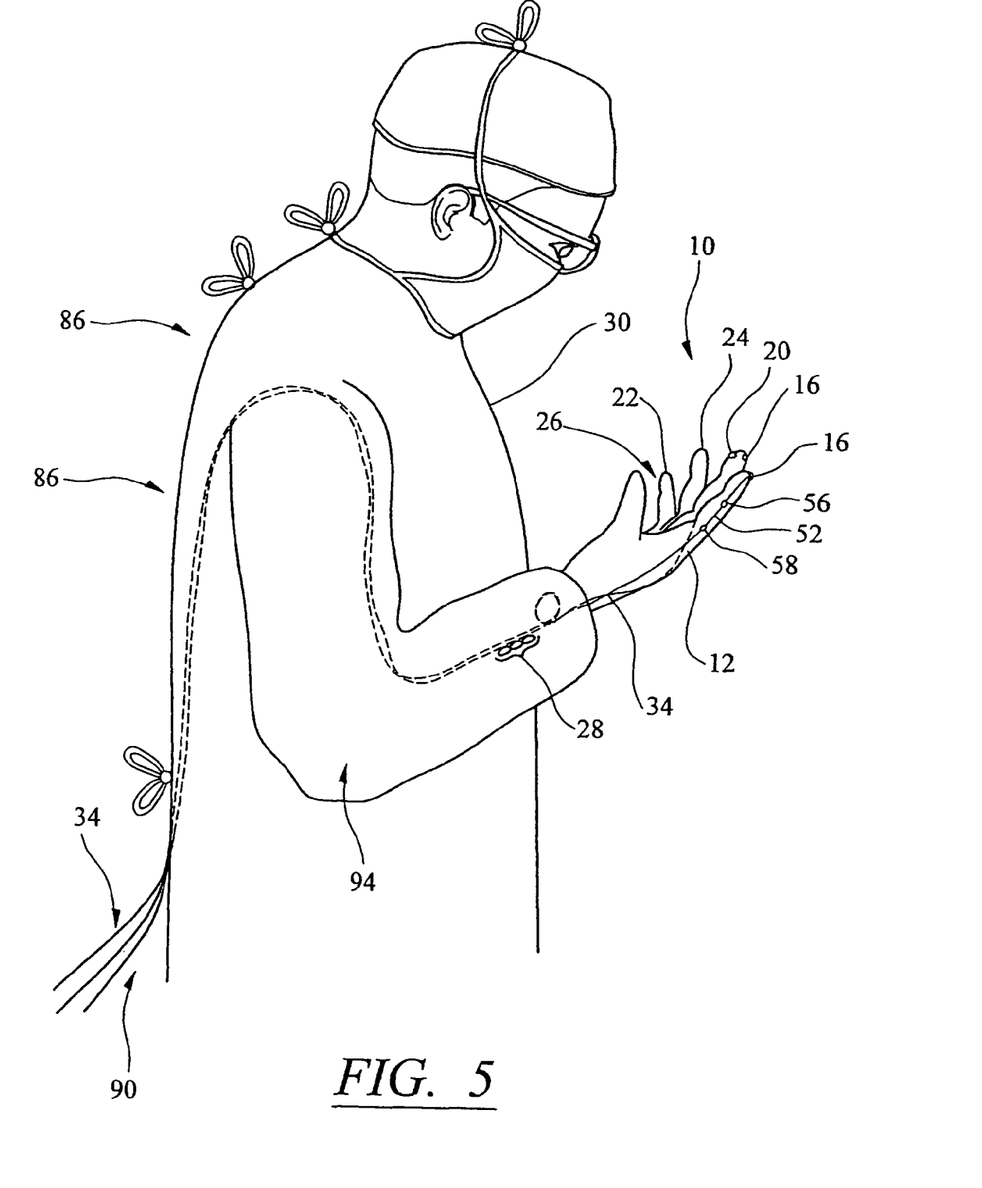
FIG. 5 is a view of a surgeon wearing the surgical glove of FIG. 1 and a surgical gown.

As shown in FIGS. 1-11, this invention is directed to a surgical system 10 formed surgical glove 12 having support systems 14 such as, but not limited to, one or more lights 16, electrical cautery 18, suction 20, irrigation 22 and ultrasonic cutting and coagulation surgical devices 23. The surgical glove 12 may include one or more of the lights 16, electrical cautery 18, suction 20, irrigation 22 and ultrasonic cutting and coagulation surgical devices 23 positioned on distal ends 24 of fingers 26 of the surgical glove 12. The support systems 14 may be controlled with switches 28 positioned on the fingers 26 upon which each support system 14 is positioned. The switches 28 may be operable with the thumb 49 on the human hand upon which the surgical glove 12 is attached. The surgical system 10 may also include a surgical gown 30 having a connection system 32 for attaching support conduit 34 of the support systems 14 to the surgical gown 30. The surgical system 10 enables a surgeon to have a plurality of support systems 14 immediately available and reduces entanglement problems endemic with conventional systems. The switches 28 may also be placed on the surgical gown 30, as shown in FIG. 5.

Figure 1:
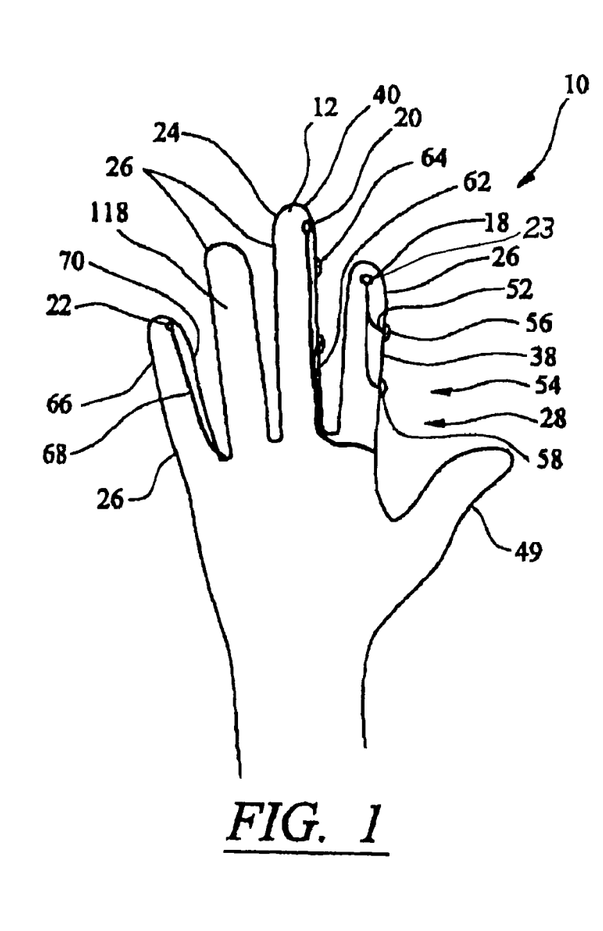
FIG. 1 is a view of a palm, otherwise referred to as a volar aspect, of a right glove of the surgical system.
Figure 2:
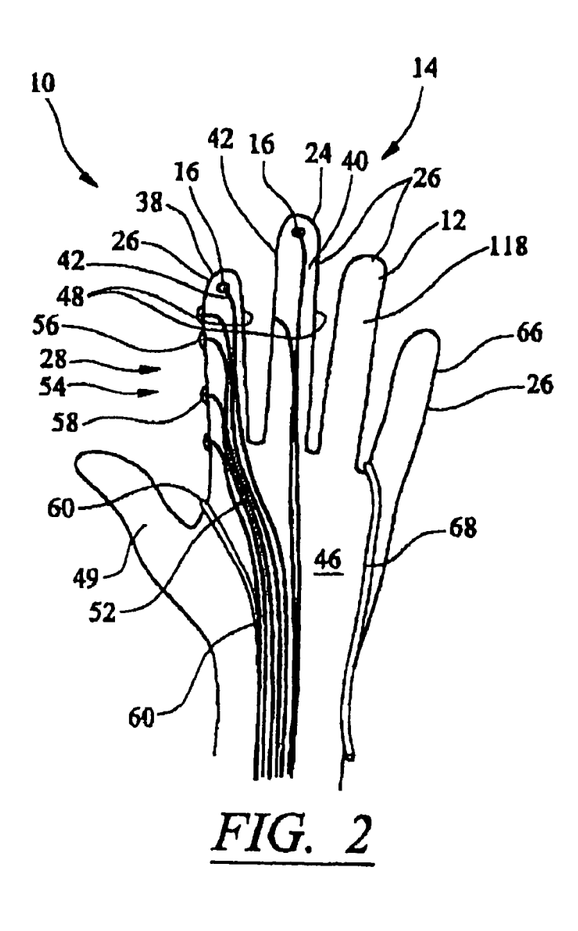
FIG. 2 is a view of a back of the glove shown in FIG. 1, otherwise referred to as a dorsal aspect.

As shown in FIGS. 1 and 2, the surgical glove 12 may be configured to be fit onto a human hand. The surgical glove 12 may be configured to fit onto a right hand or a left hand. The surgical glove 12 may be formed from any appropriate flexible material such as but not limited to latex and non-latex materials. The surgical glove 12 may be disposable or reusable. The surgical glove 12 may also include antibacterial agents, such as a coating or other appropriate applications. The glove may be able to be sterilized with conventional techniques. The glove may be usable to be sterilized with conventional techniques.

The surgical glove 12 may include one or more support systems 14, such as, but not limited to, one or more lights 16, electrical cautery 18, suction 20, irrigation 22 and ultrasonic cutting and coagulation surgical devices 23. The support systems 14 may be attached to the surgical glove 12 in numerous configurations to optimize the configuration for a surgeon such that the systems 14 are located for facility of use and in a position where the systems 14 are unlikely to obstruct or conflict with the general use of the surgeon's hand or the use of surgical instruments. In at least one embodiment, the support systems 14 are integrally formed with the surgical glove 12. The support systems 14 may be nonremovably attached to the glove 12 such that the support systems 14 may remain proximate to the surgeon's hand and distal to the surgeon's wrist thereby eliminating the need for the surgeon to retrieve the implement from resting on a surgical field. In other embodiments, the support systems 14 may be removably attached to the surgical glove 12. In yet another embodiment, the support systems 14 may be positioned between layers of material forming the surgical glove 12. The support systems 14 may be attached to internal or external aspects of the surgical glove 12.

As shown in FIGS. 1-4, the support systems 14 may be attached to the surgical glove 12 such that the one or more of the support systems 14 is attached to the distal end 24 of a finger 26 of the surgical glove 12. For instance, the one or more light sources 16 may be attached to a distal end 24 of a finger 26. In at least one embodiment, a light source 16 may be attached to a distal end 24 of an index finger 38, and a light source 16 may be attached to a distal end 24 of a long finger 40. A light source 16 may be positioned at the distal end 24 of a finger 26 and on a dorsal surface of the finger 26. The light source 16 may be formed from any appropriate light source. In at least one embodiment, the light source 16 may be formed from a halogen light, a fiber optic light, or other appropriate light source. The light source 16 may be coupled to a power source via a light source support conduit 42. The light source support conduit 42 may be formed from an insulated metallic conductor, a fiber optic cable, or other appropriate device capable of supporting the light source 16. The light source support conduit 42 may be coupled to the surgical glove 12 through any appropriate means. In at least one embodiment, the light source support conduit 42 may be integrally formed with the surgical glove 12 during formation of the surgical glove 12. The light source support conduit 42 may be positioned along internal or external surfaces 44, 46, respectively. In another embodiment, the light source support conduit 42 may be positioned between layers of material forming the surgical glove 12.

The light source 12 may be controlled remotely from the surgical glove 12. In at least one embodiment, the light source 12 may be controlled at a light source control switch 48 positioned at a control center in a surgery room. The light source control switch 48 may be controlled by a surgical assistant, nurse, or other personnel. In an alternative embodiment, the light source control switch 48 may be positioned on the surgical glove 12. For instance, the light source control switch 48 may be positioned on the finger 26 upon which the light source 16 is attached. The light source control switch 48 may be positioned on a volar, ulnar aspect 50 of the finger 26. In this position, a thumb 49 on the same hand may contact the light source control switch 48 to turn the light source on and off. The light source control switch 48 may be any appropriate switch, such as, but not limited to a depression actuated switch or other appropriate switch. The light source control switch 48 may be sized and positioned such that inadvertent activation by an adjacent finger is unlikely. Typically, such inadvertent activation is unlikely due to the distance created between adjacent fingers by the knuckles and the need to oppose the thumb to the switch to activate the switch. In yet another embodiment, a light source control switch 48 may be positioned on a surgical gown 30.

As shown in FIGS. 1-4, the surgical glove 12 may also include an electrical cautery source 18 that may be attached to the distal end 24 of a finger 26 of the surgical glove 12. In at least one embodiment, an electrical cautery source 18 may be attached to a distal end 24 of an index finger 38. The electrical cautery source 18 may be formed from any appropriate electrical cautery device appropriate for use in surgical procedures. The electrical cautery source 18 may be coupled to a power source via an electrical cautery support conduit 52. The electrical cautery support conduit 52 may be formed from an insulated metallic conductor or other appropriate device capable of supporting the electrical cautery source 18. The electrical cautery support conduit 52 may be coupled to the surgical glove 12 through any appropriate means. In at least one embodiment, the electrical cautery support conduit 52 may be integrally formed with the surgical glove 12 during formation of the surgical glove 12. The electrical cautery support conduit 52 may be positioned along internal or external surfaces 44, 46, respectively. In another embodiment, the electrical cautery support conduit 52 may be positioned between layers of material forming the surgical glove 12.

The electrical cautery source 18 may be controlled with an electrical cautery switch 54. In at least one embodiment, the electrical cautery switch 54 may be positioned on the surgical glove 12, as shown in FIGS. 3 and 4. For instance, the electrical cautery switch 54 may be positioned on the finger 26 upon which the electrical cautery source 18 is attached. The electrical cautery device 18 may be positioned on a distal, volar surface of the index finger 38. The electrical cautery switch 54 may be positioned on a radial aspect 50 of the finger 26. In this position, the thumb 49 on the same hand may contact the electrical cautery switch 54 to control the electrical cautery source 18. The electrical cautery switch 54 may include a cutting switch 56 for controlling cutting operations of the electrical cautery source 18 and a coagulation switch 58 for controlling cautery operations of the electrical cautery source. In another embodiment, the electrical cautery switch 54 may be positioned on the surgical gown, and include a cutting switch 56 and a coagulation switch 58. The electrical cautery switch 54 may be any appropriate switch, such as, but not limited to a depression actuated switch or other appropriate switch. The electrical cautery switch 54 may be sized and positioned such that inadvertent activation by an adjacent finger is unlikely. Typically, such inadvertent activation is unlikely because the location of the switches requires that the thumb 49 be opposed to the switch and such position does not occur accidentally.

As shown in FIGS. 1 and 4, the surgical glove 12 may also include a suction port 20 that may be attached to the distal end 24 of a finger 26 of the surgical glove 12. In at least one embodiment, a suction port 20 may be attached to a distal end 24 of the long finger 40 of the surgical glove 12. The suction port 20 may be formed from any appropriate suction device appropriate for use in surgical procedures. The suction port 20 may be coupled to a suction source via a suction port support conduit 60. The suction port support conduit 60 may be formed from a flexible conduit or other appropriate device capable of supporting the suction port 20. The suction port support conduit 60 may be coupled to the surgical glove 12 through any appropriate means. In at least one embodiment, the suction port support conduit 60 may be integrally formed with the surgical glove 12 during formation of the surgical glove 12. The suction port support conduit 60 may be positioned along internal or external surfaces 44, 46, respectively. In another embodiment, the suction port support conduit 60 may be positioned between layers of material forming the surgical glove 12.

The suction port 20 may be controlled with a suction port control switch 62. In at least one embodiment, the suction port 20 may be controlled at a suction port control switch 62 positioned at a control center in a surgery room. The suction port control switch 62 may be controlled by an surgical assistant, nurse, or other personnel. In an alternative embodiment, the suction port control switch 62 may be positioned on the surgical glove 12. For instance, the suction port control switch 62 may be positioned on the finger 26 upon which the suction port 20 is attached. The suction port control switch 62 may be positioned on a volar, radial aspect 50 of the long finger 40. In this position, a thumb 49 on the same hand may contact the suction port control switch 62 to control the suction port 20. The suction port control switch 62 may be any appropriate switch, such as, but not limited to a depression actuated switch or other appropriate switch. In another embodiment, the suction port control switch 62 may be positioned on the surgical gown 30. The suction port control switch 62 may be sized and positioned such that inadvertent activation by an adjacent finger is unlikely. Typically, such inadvertent activation is unlikely due to the distance created between adjacent fingers by the knuckles and the need to oppose the thumb 49 to the switches to activate the switches.

A suction control port 64 may be positioned inline on the suction port support conduit 60 for controlling the amount of suction at the suction port 20. A user may cover the suction control port 64 to deliver suction to the suction port 20 and to increase the suction at the suction port 20. When the suction control port 64 is unblocked, the suction at the suction port 20 is tremendously reduced, if not ceased altogether. The suction control port 64 may be controlled by a user sealing the port 64 with the user's thumb 49 on the same hand or with the user's other hand, or in another manner. Suction at the suction port 20 may be ceased entirely by pressing tightly on the suction port support conduit 60 at the suction control port 64 or at other locations along the suction port support conduit 60 or by deactivating the suction with the suction port control switch 62.

Figure 10:
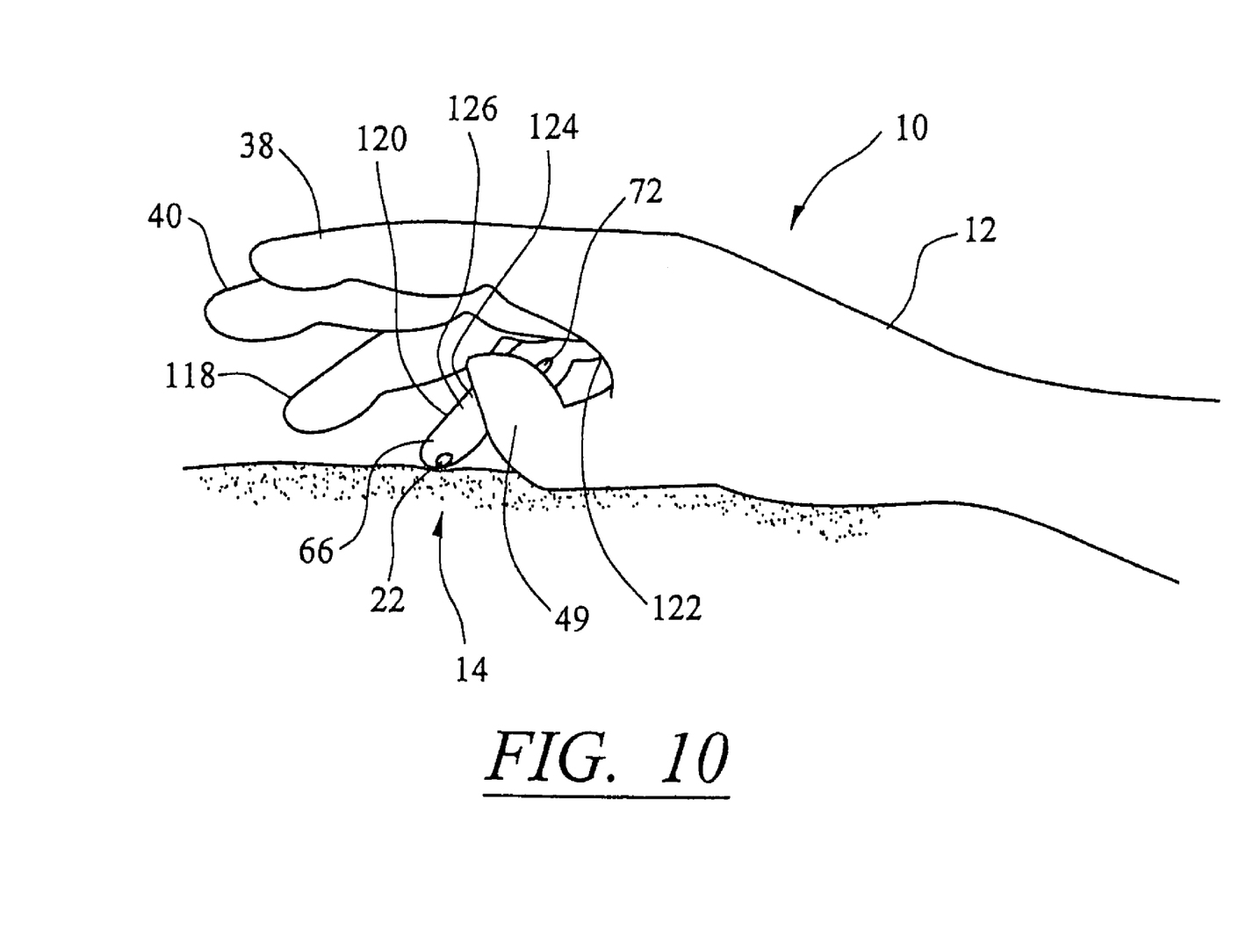
FIG. 10 is a side view of the surgical glove in which the irrigation system is positioned to be used.

As shown in FIGS. 1, 2 and 10, the surgical glove 12 may also include an irrigation source 22 that may be attached to the distal end 24 of a finger 26 of the surgical glove 12. In at least one embodiment, an irrigation source 22 may be attached to a distal end 24 of a little finger 66 of the surgical glove 12. The irrigation source 22 may be formed from any appropriate irrigation source appropriate for use in surgical procedures. The irrigation source 22 may be coupled to an appropriate surgical irrigation fluid source via an irrigation support conduit 68. The irrigation support conduit 68 may be formed from a flexible conduit or other appropriate device capable of supporting the irrigation source 22. The irrigation support conduit 68 may be coupled to the surgical glove 12 through any appropriate means. In at least one embodiment, the irrigation support conduit 68 may be integrally formed with the surgical glove 12 during formation of the surgical glove 12. The irrigation support conduit 68 may be positioned along internal or external surfaces 44, 46, respectively.

The irrigation source 22 may be controlled with an irrigation control switch 70. In at least one embodiment, the irrigation source 22 may be controlled at an irrigation control switch 70 positioned at a control center in a surgery room. The irrigation control switch 70 may be controlled by an surgical assistant, nurse, or other personnel. In an alternative embodiment, the irrigation control switch 70 may be positioned on the surgical glove 12. For instance, the irrigation control switch 70 may be positioned on the finger 26 upon which the irrigation source 22 is attached. In at least one embodiment, the irrigation control switch 70 may be positioned on the surgical glove 12. For instance, the irrigation control switch 70 may be positioned on the finger 26 upon which the irrigation source 22 is attached. The irrigation control switch 70 may be positioned on a volar, radial aspect 50 of the little finger 26. In this position, a thumb 49 on the same hand may contact the irrigation control switch 70 to control the irrigation port 22. In yet another embodiment, the irrigation control switch 70 may be positioned on the surgical gown 30. The irrigation control switch 70 may be any appropriate switch, such as, but not limited to a depression actuated switch or other appropriate switch. The irrigation control switch 70 may be formed from a control valve having a lever 72, as shown in FIG. 10, usable to turn the irrigation on and off. The lever 72 may be moved from a 3:00 position to a 6:00 position to turn irrigation on and vice versa to turn irrigation off. The irrigation control switch 70 may be sized and positioned such that inadvertent activation by an adjacent finger is unlikely. Typically, such inadvertent activation is unlikely due to the distance created between adjacent fingers by the knuckles, and the need to oppose the thumb 49 to control the lever 72.

Figure 6:
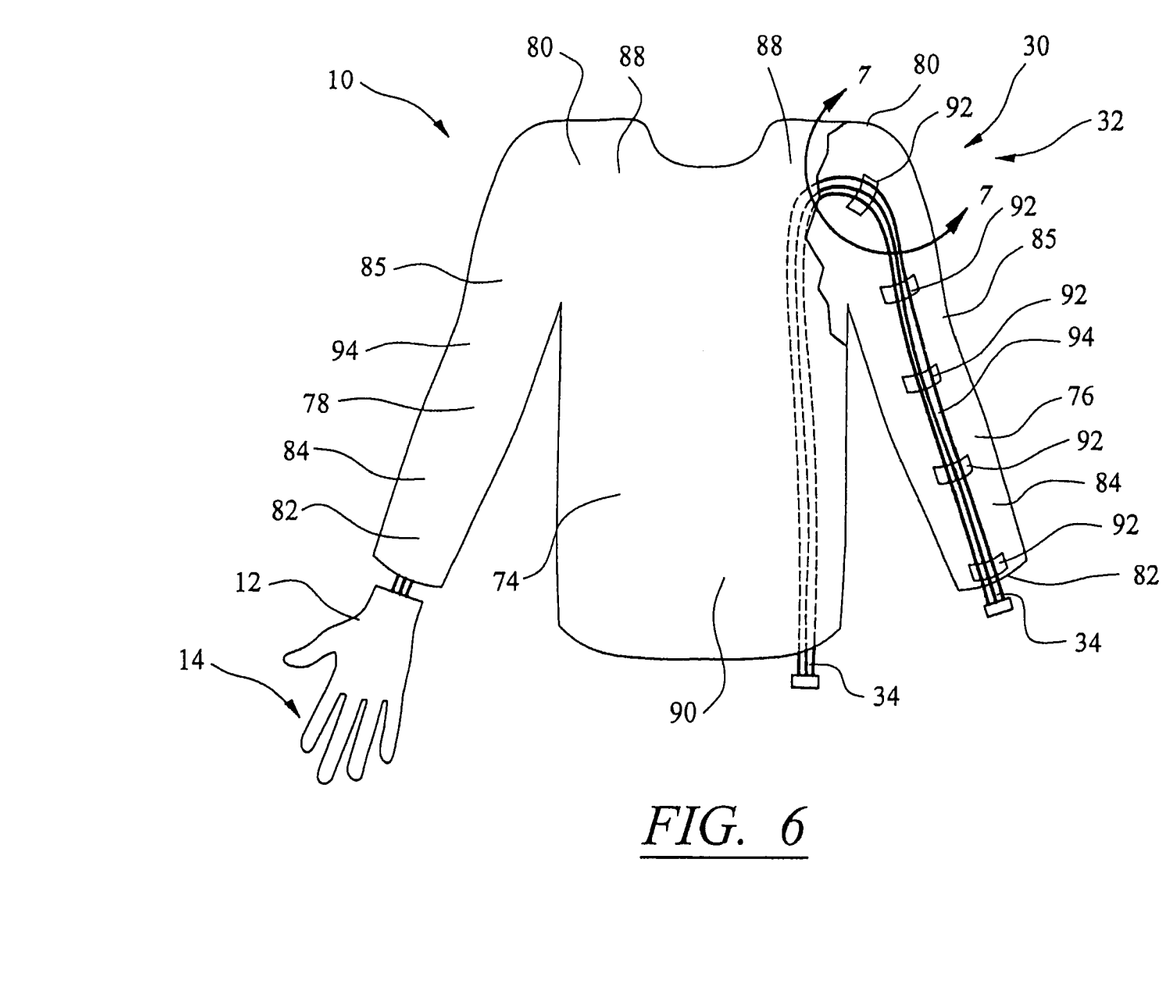
FIG. 6 is back view of a surgical gown of the surgical system with a partial cutaway of a sleeve of the surgical gown.

As shown in FIGS. 5 and 6, the surgical system 10 may include a surgical gown 30. The surgical gown 30 may include a body 74 configured to fit on a human torso and first and second sleeves 76, 78, respectively, adapted to extend from a shoulder 80 to a wrist 82 of a human. The surgical gown 30 may be formed from any appropriate material and may be formed from a disposable or reusable material. The surgical gown 30, in at least one embodiment, may include support control switches 28. The surgical gown 30 may include a connection system 32 configured to attached support conduits 34 to the surgical gown 30. In at least one embodiment, the support conduits 34 may have a length sufficient to extend from the surgical glove 12 through the surgical gown 30 and be coupled to appropriate connections within a surgery room. The support conduits 34 may, in at least one embodiment, be about eight feet in length. The support conduits 34 may be attached to systems within a surgical room with releasable connectors, such as, but not limited to, quick connectors. The support conduits 34 may be positioned in the surgical gown 30 to run along a forearm 84, upper arm 85, lateral shoulder 86, scapular 88, and lower back region 90 of a human. The support conduits 34 extend from the dorsal wrist area of the surgical glove 12 along the lateral or ulnar aspect of the surgeon's arm 84, 85 toward the shoulder 86, then posteriorly around the shoulder 86 and finally caudally down the surgeon's back, where they will be directly, appropriately connected to the appropriate connections. In at least one embodiment, the light source support conduit 42 may extend from the surgical glove 12 to an elbow region 94, where the light source support conduit 42 extends through the surgical gown 30 to be attached to an appropriate connection. In an alternative embodiment, the support conduits 34 may extend along medial or radial aspects of the arms 84, 85, into the axilla of the shoulder, over the lower margin of the scapula and cardally down the surgeon's back.

Figure 7:
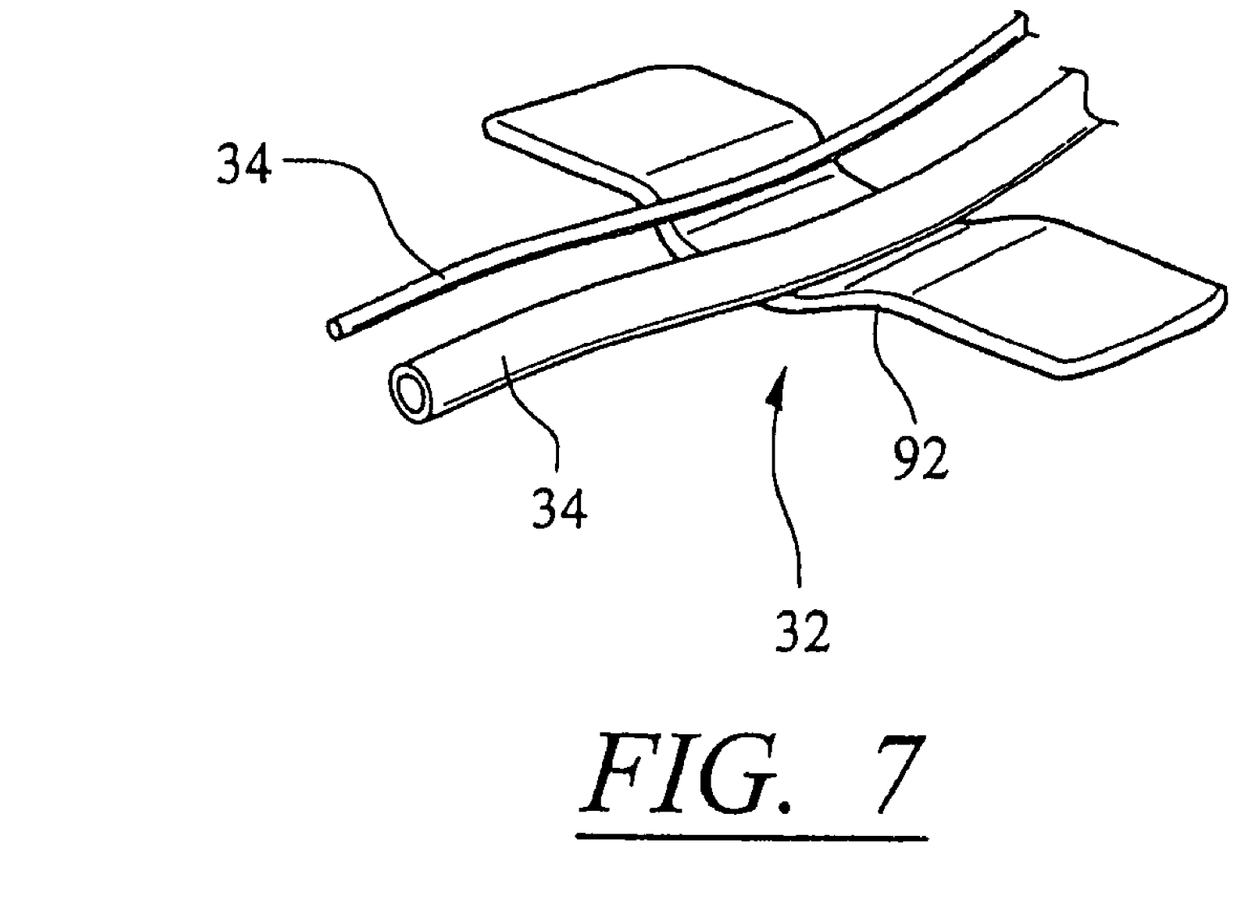
FIG. 7 is a detail view of a connection system of the surgical gown taken at line 7-7 in FIG. 6.

The connection system 32 may include attachment devices 92 on lateral aspects of the surgical gown 30 corresponding to a forearm, upper arm, lateral shoulder, scapular, and lower lateral back areas of the surgical gown to retain support conduits 34 extending from the surgical glove 12, along an arm of a human, over a shoulder of the human, and along a back of the human. The attachment devices 92 may be, but are not limited to, hook and loop connectors, such as VELCRO, releasable connectors, and other appropriate devices. In at least one embodiment, the attachments devices 92 may be formed from about ten hook and loop connectors. The attachment devices 92 effectively, visually and physically, eliminate the independent presence of electrical wires, conduits, and other support conduits, in the surgical field. In addition, the attachments devices 92 assist in preventing accidental entanglement or contamination of these entities without inhibiting the range of motion of a surgeon's arm or shoulder.

Figure 8:
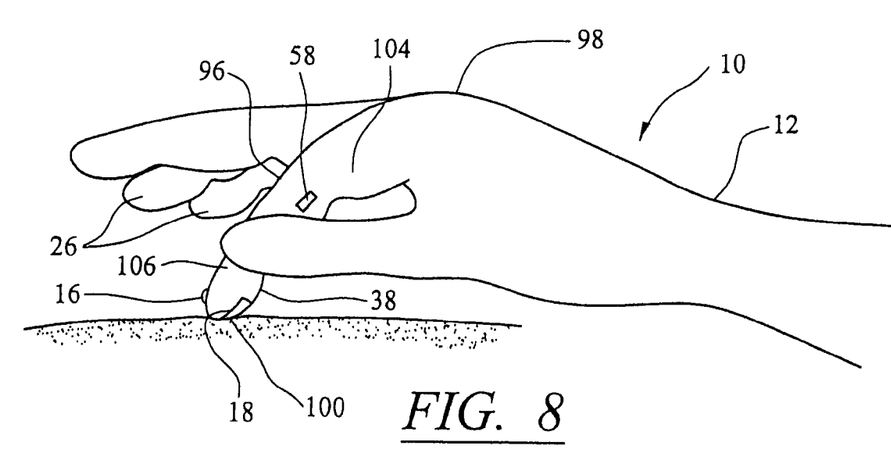
FIG. 8 is a side view of the surgical glove in which the electrical cautery is positioned to be used.

During use of the surgical system 10, a surgeon may use the various support systems 14 to assist in a surgical procedure. A surgeon may use the surgical system 10 to use the electrical cautery 18. An exemplary use of the electrical cautery device 18 is shown in FIG. 8 and is as follows. The index finger 38 may be fully extended at the inter-phalangeal joint 96 and flexed about 45 degrees at the metacarpal-phalangeal joint 98. The distal, volar aspect 100 may be contacted against surgical site. The thumb 49 may then be opposed to the index finger 38. A distal, volar, ulnar aspect 102 of the thumb 49 may be flexed and pressed against either the cutting switch 56 or the coagulation switch 58, which are located on the radial aspect 104 of the middle and proximal phalynx 106 of the index finger 38 of the surgical glove 12. Applying pressure against either the cutting switch 56 or the coagulation switch 58 may activate the respective function. Release of pressure may deactivate the respective function. The remaining fingers of the hand may be held in a relaxed fashion, flexed at the metacarpal-phalangeal joint 98 and at the inter-phalangeal joint 96. The light source 16 may be coupled to the index finger 38 to provide illumination to a suction site, as shown in FIG. 8.

Figure 9:
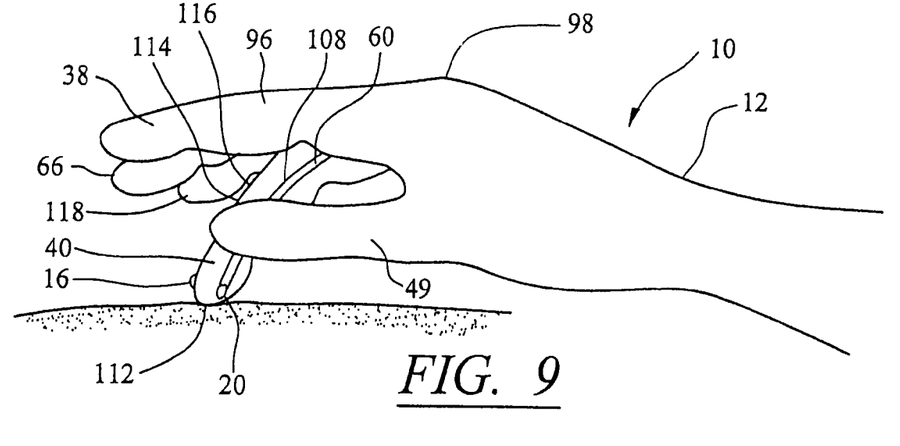
FIG. 9 is a side view of the surgical glove in which the suction system is positioned to be used.

The suction port 20, as shown in FIG. 9, may be used by extending the long finger 40 at the inter-phalangeal joint 108 and flexing about 45 degrees at the metacarpal-phalangeal joint 110 such that the distal, volar aspect 112 is directed toward the surgical site. The thumb 49 may then be opposed to the long finger 40 such that its distal, volar aspect 102 is flexed and gently pressed against the suction control port 64 located on the volar-radial aspect 114 of the middle phalynx 116 of the long finger 40. Gentle pressure on the suction control port 64 seals the port 64 and completes the circuit enabling suction to be created at the suction port 20. Exertion of a greater force against the suction control port 64 may obstruct the suction port supply conduit 60 and abruptly block all suction. Release of the pressure on the suction port supply conduit 60 allows suction to be created once again at the suction port 20 and removal of the seal at the suction control port 64 places the suction port 20 in a standby mode in which no suction is found at the suction port 20. The light source 16 may be coupled to the long finger 40 to provide illumination to a suction site, as shown in FIG. 9. While suction is being used, the remaining fingers on the hand may be relaxed and oriented as follows: the index finger 38 may be fully extended at the inter-phalangeal joint 96 and the metacarpal-phalangeal joint 98. The ring finger 118 and the little finger 66 may be flexed at the metacarpal-phalangeal joint and inter-phalangeal joint.

The irrigation source 22, as shown in FIG. 10, may be used by extending the little finger 66 at the inter-phalangeal joint 120, nearly fully extended at the metacarpal-phalangeal joint 122, and directed toward a surgical site. The thumb 49 may then be opposed to the little finger 66 and to gently turn the irrigation control switch 70, which may be positioned on the radial aspect 124 of the middle phalynx 126 of the little finger 66. The irrigation control switch 70 may be turned by applying downward pressure with the radial tip of the thumb 49 against the lever 72 of the irrigation control switch 70. Turning the lever 72 from the 3:00 position to the 6:00 position opens the irrigation control switch 70 and allows irrigation fluids to flow. Turning the lever 72 in the opposite direction, from 6:00 to 3:00, turns the irrigation flow off. Intermediary positions of the lever 72 between 3:00 and 6:00 may allow irrigation fluids to flow at slower rates than at the 3:00 position. During use of the irrigation source 22, the remaining fingers may be left in a relaxed and semi-extended position.

Figure 11:
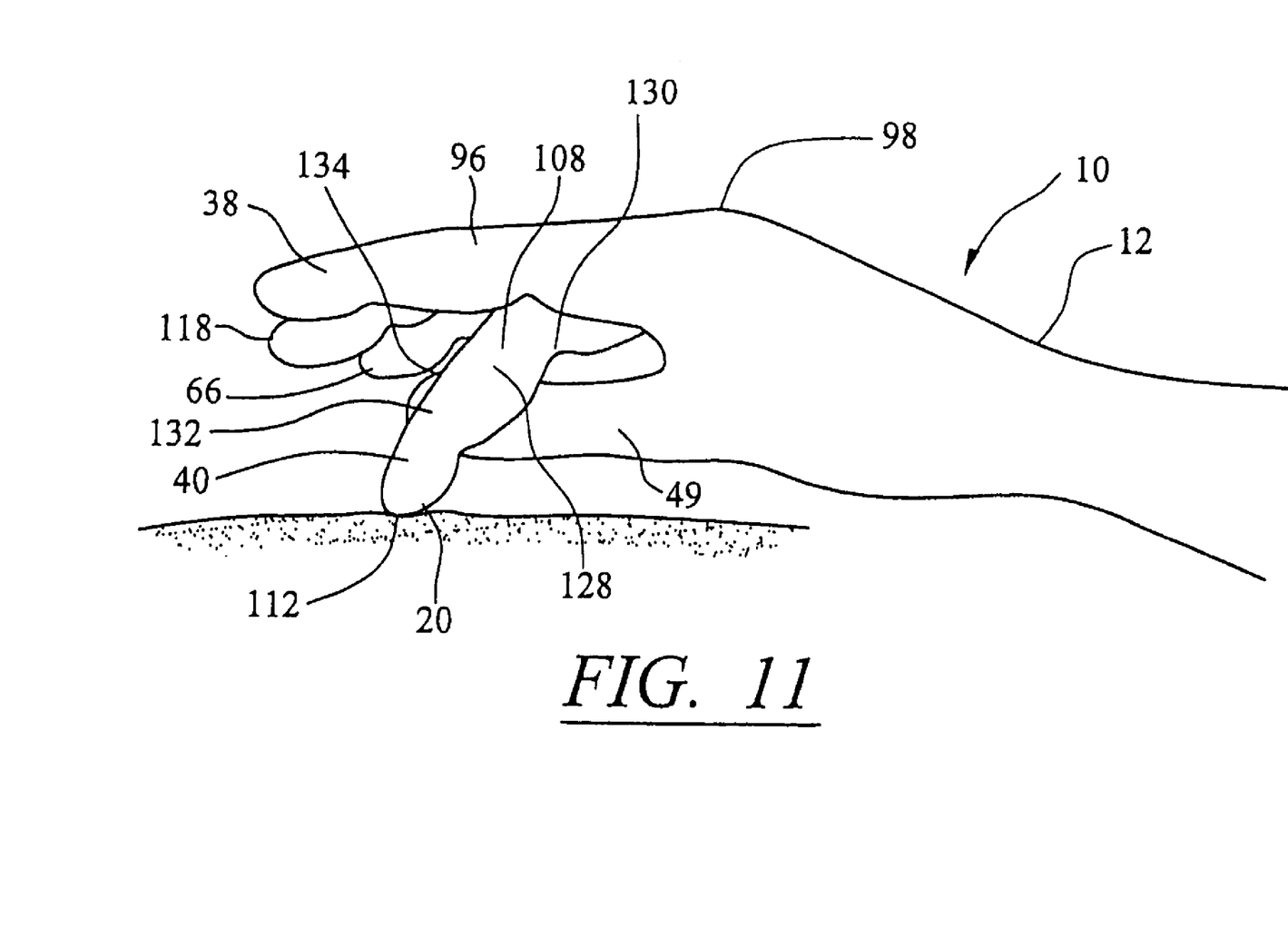
FIG. 11 is a side view of the surgical glove in which the light source is being used.

The light source control switch 48, as shown in FIG. 11, may be used by extending the index finger 38. The long finger 40 may be extended at the distal inter-phalangeal joint 128 and slightly flexed at the proximal inter-phalangeal joint 130. The distal, dorsal-ulnar aspect 102 of the thumb 49 may then be opposed to the ulnar aspect 132 of the middle phalanx 134 of the long finger 40 and pressed against the light source control switch 48. The switch 48 may be configured such that application of pressure by the thumb 49 causes the light source 16 to be turned on. Application of pressure by the thumb 49 may also turn the light source 16 off. Once activated, the light source 16 can provide illumination to a designated location by pointing the finger 38, 40 toward an area of interest. The same process may be used for light source control switches positioned on the index finger 38.

In yet another embodiment, the support systems 14 such as, but not limited to, one or more lights 16, electrical cautery 18, suction 20, and irrigation 22, may be controlled remotely with one or more wireless devices. The lights 16 and electrical cautery 18 may be powered with batteries contained within the surgical glove 12, surgical gown 30, or other appropriate location. The batteries may be any appropriate battery capable of powering the support systems 14. The batteries may or may not be rechargeable.

The invention may also be directed to a method of performing a surgical procedure in which the need to retrieve surgical implements that beforehand were rested on the surgical field is eliminated. In particular, the method may include attaching a first surgical support system 14 to a person conducting the surgical procedure before commencing the surgical procedure. The person conducting the surgical procedure may be, but is not limited to being, a surgeon or other appropriate person. At least one surgical instrument 16, 18, 20, 22, 23 may be attached to the first surgical support system 14 such that the at least one surgical instrument 16, 18, 20, 22, 23 extends proximate to a hand and at or distal to the wrist of the person to which the first surgical support system 14 is attached. The at least one surgical instrument 16, 18, 20, 22, 23 may be nonremovably attached to the glove to prevent the at least one surgical instrument 16, 18, 20, 22, 23 from being removed from the glove 12 during a surgical procedure. The first surgical support system 14 may remain attached to the person throughout the surgical procedure eliminating need to retrieve surgical implements that beforehand were rested on the surgical field. For instance, the surgeon need not rest instruments on the surgical field and constantly pick up the instruments or request the instruments from an assistant. Rather, the instruments may remain attached to the surgeon throughout the duration of the surgery. Such a method enables a surgeon to work more independently and thus maintain focus on the surgical procedure.

The method may also include attached a second surgical support system 14 to a person conducting the surgical procedure before commencing the surgical procedure. The surgical instrument 16, 18, 20, 22, 23 may be at least one light source, at least one suction port, at least one irrigation port, at least one electrical cautery source, at least one ultrasonic cutting and coagulating surgical device, or other appropriate device. The invention is not limited to only these listed devices but may be configured to include other appropriate devices as well to increase the efficiency of the surgical procedure.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A method of performing a surgical procedure, comprising:

providing a surgical glove comprising a first and a second surgical support system attached to the surgical glove, wherein the first surgical support system comprises a first surgical instrument and a first conduit, and the second surgical support system comprises a second surgical instrument and a second conduit, and wherein the first and second conduits are coupled to the glove with each of the first and second conduits traversing a mid-coronal plane of a finger of the glove, wherein each of the first and second surgical support systems are attached to the index finger, the long finger or the little finger, wherein the glove further comprises a first switch attached to the glove for controlling a first surgical support system and a second switch attached to the glove for controlling a second surgical support system, wherein said first switch is attached to a finger of the glove to which the first surgical support system is attached and said second switch is attached to a finger of the glove to which the second surgical support system is attached, and wherein a portion of each of the first and second surgical support systems and each of the first and second switches is coupled to a radial or ulnar surface of a finger of the surgical glove such that the first and second surgical instruments may be actuated by the person to which the surgical glove is attached;

attaching the glove to a person conducting a surgical procedure before commencing the surgical procedure;

wherein the first surgical support system remains attached to the person throughout the surgical procedure eliminating a need to retrieve surgical implements that otherwise rest on a surgical field; and actuating the first and second surgical instruments as part of a surgical procedure performed by the person.

2. The method of performing the surgical procedure of claim 1, further comprising at least one light source coupled to a distal, dorsal surface index finger of the surgical glove.

3. The method of performing the surgical procedure of claim 1, wherein at least one of the first and second surgical instruments comprise at least one suction port coupled to a distal, volar radial surface of a long finger of the surgical glove.

4. The method of performing the surgical procedure of claim 1, wherein at least one of the first and second surgical instruments comprises at least one irrigation port coupled to a distal, volar radial surface of a little finger of the surgical glove.

5. The method of performing the surgical procedure of claim 1, wherein at least one of the first and second surgical instruments comprises at least one electrical cautery source coupled to a distal, volar surface of an index finger of the surgical glove.

6. The method of performing the surgical procedure of claim 1, wherein the first and second surgical instruments are selected from the group consisting of at least one suction port, at least one irrigation port, at least one electrical cautery source and at least one ultrasonic cutting and coagulating surgical device.

7. The method of performing the surgical procedure of claim 1, wherein the first and second switches are controllable with a thumb of the person of a hand upon which the surgical glove is fitted.

8. The method of performing the surgical procedure of claim 1, wherein the first switch comprises an electrical cautery switch positioned on a volar, radial aspect of an index finger of the surgical glove.

9. The method of performing the surgical procedure of claim 1, wherein the first switch comprises a suction port control switch positioned on a volar, radial aspect of a long finger of the surgical glove.

10. The method of performing the surgical procedure of claim 1, wherein the first switch comprises an irrigation switch attached to a volar, radial aspect of a little finger of the surgical glove.

11. The method of performing the surgical procedure of claim 2, further comprising a light source control switch positioned on a volar, ulnar aspect of a finger on which a light source is attached.

12. The method of performing the surgical procedure of claim 1, further comprising:

attaching a surgical gown to which the first surgical system is attached to the person, wherein the surgical gown is formed from a body adapted to fit onto a torso of a human, a first sleeve extending from the body and sized to extend from a shoulder of the human to a hand of the human, a second sleeve extending from an opposite upper corner of the body and sized to extend from a shoulder of the human to a second hand of the human; and a connection system for attaching said first and second support conduits to the surgical gown.

13. The method of performing the surgical procedure of claim 12, wherein attaching the surgical gown to which the first surgical system is attached to the person wherein the surgical gown comprises attachment devices on lateral aspects of forearm, upper arm, lateral shoulder, scapular, and lower lateral back areas of the surgical gown to retain support conduits extending from the glove, along an arm of a human, over a shoulder of the human, and along a back of the human.

14. A method of performing a surgical procedure of claim 12, comprising:

wherein the gown and glove remain attached to the person throughout the surgical procedure eliminating need to retrieve surgical implements that otherwise rest on a surgical field.

15. The method of performing the surgical procedure of claim 11, wherein the surgical glove further comprises a third surgical support system attached to the surgical glove, wherein the third surgical support system comprises a third surgical instrument, wherein the glove further comprises a third switch attached to the glove for controlling a third surgical support system, and wherein a portion of the third surgical support systems and the third switch is coupled to a volar surface of a finger of the surgical glove such that the third surgical instruments may be actuated by the person to which the surgical glove is attached.

16. The method of performing the surgical procedure of claim 1, wherein the first surgical instrument is at least one electrical cautery source and the second surgical instrument is selected from the group consisting of at least one suction port, at least one irrigation port, at least one ultrasonic cutting and coagulating surgical device.

17. The method of performing the surgical procedure of claim 16, wherein the surgical glove further comprises a third surgical support system attached to the surgical glove, wherein the third surgical support system comprises a third surgical instrument, wherein the glove further comprises a third switch attached to the glove for controlling a third surgical support system, and wherein a portion of the third surgical support systems and the third switch is coupled to a volar surface of a finger of the surgical glove such that the third surgical instruments may be actuated by the person to which the surgical glove is attached.

18. The method of performing the surgical procedure of claim 17, wherein the first, second and third switches are controllable with a thumb of the person of a hand upon which the surgical glove is fitted.

19. The method of performing the surgical procedure of claim 17, wherein the second surgical instrument is at least one suction port and the third surgical instrument is selected from the group consisting of at least one light source, at least one irrigation port, at least one ultrasonic cutting and coagulating surgical device.

20. The method of performing the surgical procedure of claim 19, wherein the third surgical instrument is at least one irrigation port and the first, second and third switches are controllable with a thumb of the person of a hand upon which the surgical glove is fitted.

21. A method of performing a surgical procedure, comprising:

providing a surgical glove comprising a first and a second surgical support system attached to the surgical glove, wherein the first surgical support system comprises a first surgical instrument and a first conduit, and the second surgical support system comprises a second surgical instrument and a second conduit, wherein the glove further comprises a first switch attached to the glove for controlling a first surgical support system and a second switch attached to the glove for controlling a second surgical support system, wherein said first switch is attached to a finger of the glove to which the first surgical support system is attached and said second switch is attached to a finger of the glove to which the second surgical support system is attached, and wherein a portion of each of the first and second switches is coupled to a radial or ulnar surface of a finger of the surgical glove such that the first and second surgical instruments may be actuated by the person to which the surgical glove is attached;

attaching the glove to a person conducting a surgical procedure; and actuating the first and second surgical instruments as part of the surgical procedure performed by the person.

22. The method of performing the surgical procedure of claim 12, further comprising:

attaching the first and second conduits to the connection system of the surgical gown.

* * * * *